United States Patent [19]

Smith

[11] Patent Number: 4,844,608

[45] Date of Patent: Jul. 4, 1989

[54] SOLUTION MONITORING PROCEDURE

[75] Inventor: Craig G. Smith, North Plainfield, N.J.

[73] Assignee: American Telephone and Telegraph Company AT&T Bell Laboratories, Murray Hill, N.J.

[21] Appl. No.: 29,040

[22] Filed: Mar. 23, 1987

[51] Int. Cl.$^4$ ............................................. G01N 21/41
[52] U.S. Cl. .................................................... 356/136
[58] Field of Search ........................ 356/136, 135, 128

[56] References Cited

U.S. PATENT DOCUMENTS 4,451,147  5/1984  Dobes et al. ........................ 356/135

Primary Examiner—Richard A. Rosenberger
Attorney, Agent, or Firm—Walter G. Nilsen

[57] ABSTRACT

Processes are described in which solution composition is monitored by extremely accurate measurements of index of refraction involving measurement of reflectivity from a glass-solution interface. A particularly useful application is the swelling operation in metallizing polymer surfaces where dimethylformamate-water solution is contacted with the polymer surface to produce the swelling. Accurate, continuous control of the solution composition is necessary to insure optimum amount of swelling.

10 Claims, 3 Drawing Sheets

SOLUTION MONITORING PROCEDURE

TECHNICAL FIELD

The invention involves a process for making an article where the composition of a multicomponent solution used in the process is monitored using highly accurate index of refraction measurements.

BACKGROUND OF THE INVENTION

Various types of chemical solutions are used extensively in the fabrication of devices and articles. Typical examples are plating solutions, solutions used to etch surfaces or holes, solutions used to prepare surfaces for various processing, etc. The success of these processes often depends critically on the exact composition of these solutions as well as other process parameters such as temperature, contact time, etc. Highly desirable is a continuous procedure for monitoring solution composition so as to insure close control of the process.

Indeed, in many modern technological processes, rapid, continuous response to composition changes is a necessity to avoid extensive loss of product and to prevent the production of defective product.

A particular example may be used in illustrating the importance of close control of solution composition in some processes. Solutions of dimethylformamide in water are used to treat polymer surfaces prior to metallization in the fabrication of substrates for circuit boards. Close control of solution composition is of critical importance. Too high a concentration of dimethylformamide in water leads to a brittle surface; too low a concentration produces insufficient swelling and often weak bonding of metal to polymer surface. Close control of solution concentration as well as temperature and exposure time yields smooth, well-bonded metallic layers suitable for use in circuit boards.

Particularly useful is a method of continuously monitoring solution composition so as to insure correct composition of solution at all times. Also useful is a feedback system to continuously and automatically adjust solution composition to a predetermined value. Various multicomponent solutions are of interest including 2-component solutions, 3-component solutions and larger-component solutions.

SUMMARY OF THE INVENTION

The invention is a process for fabricating a device, said process involving a solution, in which the composition of the solution is monitored by a special refractive index measurement procedure. The measurement procedure involves use of a dual wavelength technique to provide intrinsic stability and a glass surface in contact with the solution to provide extremely high sensitivity. The procedure is designed to provide extremely accurate index of refraction measurements over the narrow index range of interest in solution composition measurements. The index range is fixed by suitable selection of glass material, angle of incidence and wavelength. Two wavelengths $\lambda_1$ and $\lambda_2$ are selected so as to provide partial reflection of one wavelength ($\lambda_1$) and complete reflection of the other wavelength ($\lambda_2$). The second wavelength ($\lambda_2$) provides a reference beam to correct for fluctuations in various parameters such as source intensity. The first wavelength ($\lambda_1$) is used to measure index of refraction. Such a system provides a monitoring scheme where solution composition is a function of reflected light intensity. Such close control of solution composition yields excellent results particularly for the swelling operation in metallizing polymer surfaces for circuit boards or other uses.

DETAILED DESCRIPTION

Figure 1:
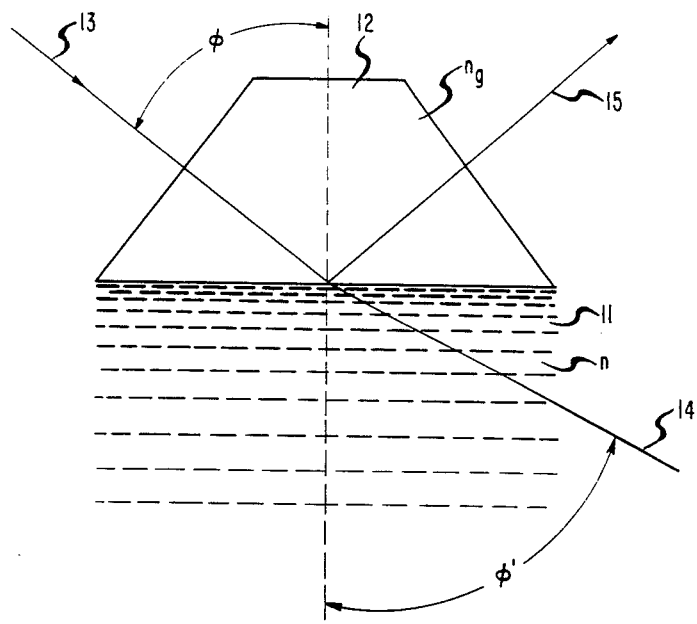
FIG. 1 shows an optical ray diagram of the solution composition monitoring system.

The invention is based on the discovery that the index of refraction of a solution can be measured very accurately and in a form highly convenient for process monitoring by putting the solution in contact with one surface of a prism, adjusting the angle of incidence of the light beam on this prism surface so that small changes in the index of refraction of the liquid result in changes in the intensity of the reflected light. As the index of the liquid approaches the index of the glass prism, more and more light is refracted into the liquid and less reflected away from the liquid (see FIG. 1). A double beam arrangement is used in the measuring process with two beams of light or radiation at different wavelengths. The first beamm of light with wavelength $\lambda_1$ is used to measure the index of refraction of the solution as described above. The other beam of light with wavelength $\lambda_2$ is used as standard or reference beam to correct for various parameter variations such as variation in source intensity, detector sensitivity, amplifier gain, surface film formation on the prism, etc. The temperature of the solution is also measured to correct for variations of parameters caused by temperature changes.

The standard beam is largely reflected at the glass-liquid interface with little or no refraction into the liquid. This is usually referred to as total reflection of the beam. In practice, reflection is only about 95 percent due to various imperfections in the glass-liquid interface such as scratches, dust, etc. For convenience, the reflection is referred to as total although its important characteristic is its independence from variations in the index of refraction of the liquid.

The invention is conveniently described in terms of the design of the apparatus used to measure the composition of the solution. Two wavelengths are used in the measurement, one wavelength being partially reflected from a solid-liquid interface and the other wavelength totally reflected and used as an intensity reference. The reflectivity of the partially-reflected beam depends on the index of refraction of the liquid. Various arrangements can be used to accommodate the two wavelengths. Two light beams might be used as one beam containing the two wavelengths. Also, a beam of light with a range of wavelengths might be used with proper selection of each wavelength (e.g., by the use of optical filters) at the detector.

The general structure and measurement philosophy applies to a large variety of solutions including binary solutions and solutions with more than two components. For purposes herein, solutions with more than two components are referred to as multicomponent solutions. Particular design features depend on the range of index which needs to be measured to monitor the composition of the solution.

In order to provide a concrete example, a dimethylformulatewater solution will be used with composition at about 86±3 volume percent dimethylformamate.

The index of refraction at ambient temperatures is about 1.42. The range of index around this index which is useful for composition control at ordinary ambient temperatures is about ±0.005. The procedure is designed to insure maximum index sensitivity in this index range.

In applying the process to a specific solution, parameters are selected to insure accurate measurement over the index range of interest. This index range depends on the solution and how the index changes with composition and the expected temperature variations and how it affects the index. Among the parameters to be selected are the index of refraction and dispersion of the glass, the angle of incidence of the measuring and reference beams and the wavelengths of the measuring and reference beams.

The various parameters may be selected in a number of ways. It is usually most convenient to first select the glass (or transparent substance) used in the prism in contact with the solution. Although a number of transparent substances can be used including plastic, single crystal, etc., glass is most convenient and is usually not affected by the solution being measured. Optical quality glass is most preferred. Typical optical materials are quartz, flint glass and Crown glasses. A large variety of optical materials including optical glasses are found in various trade catalogs including "The Optical Purchasing Directory", Book 2, The Optical Publishing Co., Inc., Pittsfield, Mass. It should be remarked that the glass denoted as SF-11 (made by Schlott or Ohara), with index 1.785 at the sodium D line, Abbe Number 25.7 is useful for a large variety of applications.

In order to have partial reflection of the light beam from the glass-solution interface, the index of the glass should be at least 0.1 units higher than the index of the solution being measured. This is to insure reasonable reflections at the glass-solution interface. It is preferred that the index of the glass be not mroe than about 0.6 units greater than the solution because of the difficulty of obtaining any reflection of the glass-solution interface at reasonable angles of incidence. Generally, a glass index about 0.3 to 0.4 units greater than the solution is most convenient.

Second, the angle of incidence is chosen to yield reasonable reflection intensity at the solution composition of interest. It is preferred that this reflection intensity change significantly with composition and that this change be approximately linear with solution composition. The wavelength of the measuring ($\lambda_1$) and reference beam ($\lambda_2$) are chosen so that the measuring beam is partially reflecting at the interface and the reference beam is completely reflecting at the glass-liquid interface.

A calculation is carried out to determine the nature of the function of reflected intensity vs. composition of the solution. The calculation is best explained by reference to the setup 10 in FIG. 1. The solution 11 being measured has an index of refraction denoted by n and the glass prism 12 an index of refraction denoted by $\eta_g$. The incident light beam 13 has an angle of incidence of $\phi$ and the angle of refraction of the refracted beam 14 is denoted by $\phi'$. The angle of incidence $\phi$ is selected to produce roughly 50 percent reflection for $\lambda_1$ near the midpoint of the index range to be controlled and to produce roughly linear response to composition changes. Simultaneously, near total reflection is desired for $\lambda_2$ over the entire range of solution composition and temperature. To achieve this result, calculations are made of the reflection coefficient at the different indexes of refraction exhibited by the solution at the compositions of interest and likely solution temperatures from the reflected beam 15. Both the measuring beam and reference beam are usually incorporated in the incident beam; the measuring beam at a wavelength where only partial reflection occurs and the reference beam a wavelength where total reflection occurs.

The intensity of the reflected light beam can be characterized theoretically by the use of the Fresnel reflection coefficients. Light is characterized by the phase and amplitude of the electric field in two perpendicular planes. The plane defined by the incident and reflected beams is deonted by the subscript p, while the plane perpendicular to this is denoted by the subscript s. The general theory applies to an absorbing medium, and the reflection coefficients are complex variables. However, for the present case, both the glass prism and the solutions are assumed to be lossless dielectrics the simplified coefficients are used. The ratio of the amplitude of the reflected and incident electric fields are $r_p$ and $r_s$ for p and s polarized light:

$$r_s = \frac{-\sin(\phi - \phi')}{\sin(\phi + \phi')} \qquad (1)$$

$$r_p = \frac{\tan(\phi - \phi')}{\tan(\phi - \phi')} \qquad (2)$$

The angle of refraction $\phi'$ is related to the angle of incidence $\phi$ by Snell's law:

$$\eta_g \sin(\phi) = \eta \sin(\phi'). \qquad (3)$$

The intensities of the reflected beams are obtained by squaring the amplitude reflection coefficients and are denoted as $R_p$ and $R_s$.

For unpolarized light and no polarization selection in the detector system, the reflection coefficient is given by $$R = 0.5 (r_p^2 + r_s^2). \qquad (4)$$

The refractive indices of both the glass prism and the solution are functions of wavelength. The refractive index of the solution is a function of temperature and composition. For design purposes, the temperature dependence of the glass is neglected.

For design purposes, the intensity of the reflected measuring beam is calculated as a function of index of refraction for indices of interest in measuring composition of the solution. This is done for various angles of incidence $\phi$ to insure a reasonably linear relation between composition and reflection intensity and some reasonable change in reflection intensity with composition.

Figure 2:
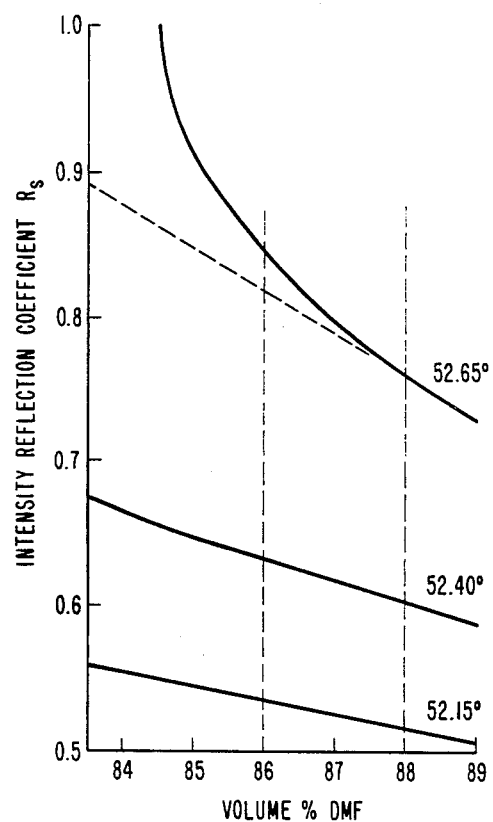
FIG. 2 shows a calibration of light intensity vs. solution composition for dimethylformamide in water solution.

A typical set of curves is shown in FIG. 2 where intensity reflection coefficient is plotted as a function of composition of a dimethylformamide-water solution. Three curves are shown as three different angles of incidence $\phi$. At $\phi = 52.65$ degrees. The R vs. composition curves is highly nonlinear and at $\phi = 52.15$ degrees, the variation of R with composition is not very great.

At a value of $\phi = 52.40$ degrees, the curve is close to linear and the change of R with composition is reasonably large. Thus, for angles of incidence close to $\phi = 52.40$ degrees, the dependence of R on composition seems satisfactory composition measurement. Also, calculations for the reference beam at a wavelength of 486 nm show complete reflection over the composition range of interest and the solution temperature range of interest.

Figure 3:
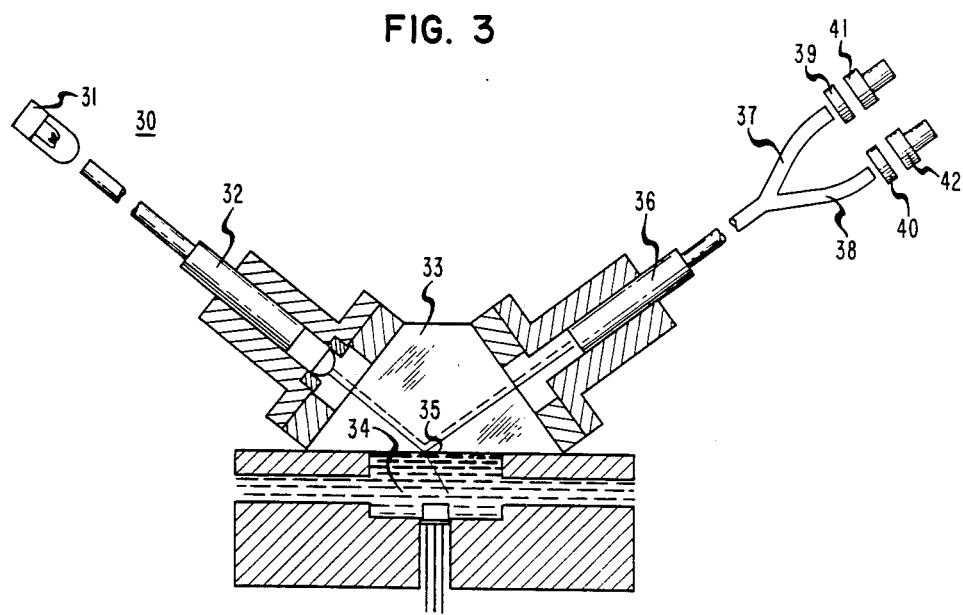
FIG. 3 shows a diagram of a typical apparatus for monitoring solution composition in accordance with the invention.

FIG. 3 shows an apparatus used to monitor the composition of a solution in accordance with the invention. It essentially measures index of refraction of the solution by the intensity of the light reflected from the glass-solution interface. The apparatus 30 is composed of a light source 31, a lens and aperture system to produce collimated light 32, a glass prism 33 which interfaces with the solution being measured 34 at an interface 35 where some of the light is reflected and then collected at another lens system 36. The collected light is divided into two parts, one 37 going to a detection system that responds only to light at the measuring-beam wavelength (810 μm in this example) and one 38 responding only to light at the reflected-beam wavelength (450 μm in this example). Light filters 39 and 40 are often used in front of the light detectors to accomplish this end.

Figure 4:
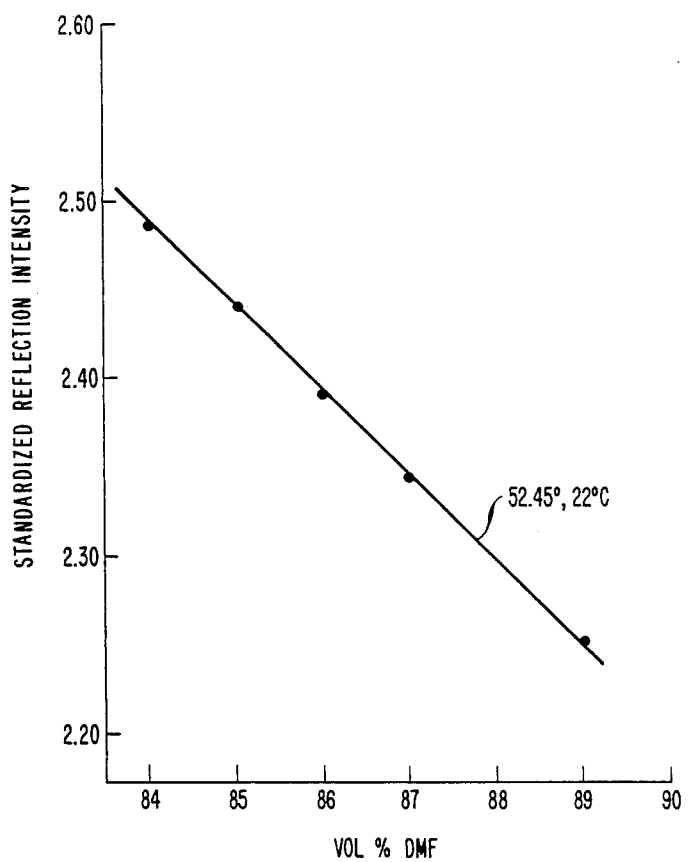
FIG. 4 shows data on the refraction intensity vs. composition in a dimethylformamate in water solution.

After fixing the parameters for a particular application, it is often advantageous to produce a calibration curve both for added accuracy and to confirm the near linear relationship between reflected intensity and composition. Measurements are made on solutions of known composition. A standarized reflection intensity is used which is the intensity of the measuring beam (at 810 μm in this case) divided by the intensity of the standard beam (450 μm in this case) in the calibration measurements and subsequent concentration measurement. A typical calibration measurement is shown in FIG. 4 for 22° C. Other calibration curves may be measured for other temperatures. By suitable measurement of standarized reflection intensity and temperature, the solution composition may be determined. Also, a feedback control system is advantageously used with this system.

Solutions with more than two components can be measured with additional information. For example, densitometer measurements may be used in conjunction with the index of refraction measurements to provide the additional information or various other types of measurements calorimetry, etc.) may be used. Also, various assumptions may be made such as two components remain in the same ratio to provide the additional information for the third component.

Processes carried out using the inventive process yield excellent results including extremely uniform and constant amount of swelling and uniform surface plating. In addition, electroless metal plating (e.g., copper or nickel) carried out on such surfaces after suitable swelling yields excellent metallized surfaces suitable for a variety of applications including for electronic devices, printed wiring boards, as well as cosmetic or jewelry articles.

What is claimed is:

1. A process for producing an article comprising the step of contacting a multicomponent solution with a pair of the article or contacting a reaction product of the multicomponent solution and at least one reactant in which the composition of the multicomponent solution is monitored by measuring the index of refraction of the multicomponent solution characterized in that the measurement of the index of refraction of the multicomponent solution comprises the steps of:

a. directing at least one light beam onto an interface between a transparent solid and the multicomponent solution, said light beam comprising a first radiation with a first wavelength and a second radiation with a second wavelength different from the first wavelength; the first wavelength of the first radiation selected so that a portion of said first radiation is reflected and a portion of said first radiation is refracted at the interface in which the portions of the first radiation that are reflected and refracted depend on the index of refraction of the multicomponent solution and the second wavelength of the second radiation is selected so that the second radiation is substantially totally reflected from the interface, such substantial total reflection being substantially independent of the index of refraction of the multicomponent solution; and b. measuring the intensity of the first radiation with the first wavelength and the intensity of the second radiation with the second wavelength.

2. The process of claim 1 in which the multicomponent solution is a two-component solution.

3. The process of claim 1 in which the step is contacting the multicomponent solution with a surface of the article.

4. The process of claim 3 in which the surface is a polymer surface.

5. The process of claim 3 in which the multicomponent solution comprises dimethylformamate in water.

6. The process of claim 3 in which the transparent solid is a glass in the form of a prism.

7. The process of claim 6 in which the index of refraction of the glass is from 0.1 to 0.6 units higher than the multicomponent solution.

8. The process of claim 7 in which the index of refraction of the multicomponent solution is about $1.42 + 0.01$.

9. The process of claim 8 in which the glass has index refraction of $1.785 + 0.020$ at the sodium D line and an Abbe Number of $25.7 + 0.3$.

10. The process of claim 6 in which the surface is electrolessly metal plated.

* * * * *